United States Patent
Brommersma et al.

(10) Patent No.: US 6,893,441 B2
(45) Date of Patent: May 17, 2005

(54) UROLOGICAL ELECTROSURGICAL RESECTOSCOPE

(75) Inventors: Pieter Brommersma, Bargteheide (DE); Felix Nussbaum, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 54 days.

(21) Appl. No.: 10/111,197
(22) PCT Filed: Aug. 4, 2001
(86) PCT No.: PCT/EP01/09045
 § 371 (c)(1), (2), (4) Date: Jun. 4, 2002
(87) PCT Pub. No.: WO02/17808
 PCT Pub. Date: Mar. 7, 2002

(65) Prior Publication Data
 US 2003/0144661 A1 Jul. 31, 2003

(30) Foreign Application Priority Data
Aug. 26, 2000 (DE) .................. 100 42 097

(51) Int. Cl.⁷ .................. A61B 18/18
(52) U.S. Cl. .................. 606/46; 600/105; 600/106; 600/107
(58) Field of Search .................. 606/27–29, 37–41, 606/45–50; 607/101, 105, 106, 107

(56) References Cited

U.S. PATENT DOCUMENTS 4,726,370 A * 2/1988 Karasawa et al. ............ 606/46
4,917,621 A   4/1990 Grossi et al.
4,919,131 A   4/1990 Grossi et al.

FOREIGN PATENT DOCUMENTS

| DE | 39 17 583 A1 | 3/1990 |
| DE | 39 18 316 A1 | 3/1990 |
| FR | 2 400 351 A | 3/1979 |

OTHER PUBLICATIONS

WO 96/23449, Electro–Surgical Tissue Removal, Publication Date Aug. 8, 1996.

* cited by examiner

Primary Examiner—Rosiland Rollins
(74) Attorney, Agent, or Firm—Rankin, Hill, Porter & Clark LLP

(57) ABSTRACT

A urological resectoscope having an axially extending shaft tube, the proximal end thereof being fixed to a main body. A sliding body is proximally positioned in relation to the main body, and can slide in a parallel manner in relation to the axis thereof. The sliding body includes a receiver, a fixing device and a contacting device. An electrode that can be subjected to a high frequency, including a rigid electrode carrier having one external, insulated conductive wire, can be positioned in the resectoscope such that it can axially slide beyond the distal end of the shaft tube. In the assembly position, the electrode carrier extends through the shaft tube and the main body into the receiver, and can be fixed by the fixing device and contacted by the contacting device. The fixing device is proximally arranged in relation to the contacting device on the sliding body.

6 Claims, 1 Drawing Sheet

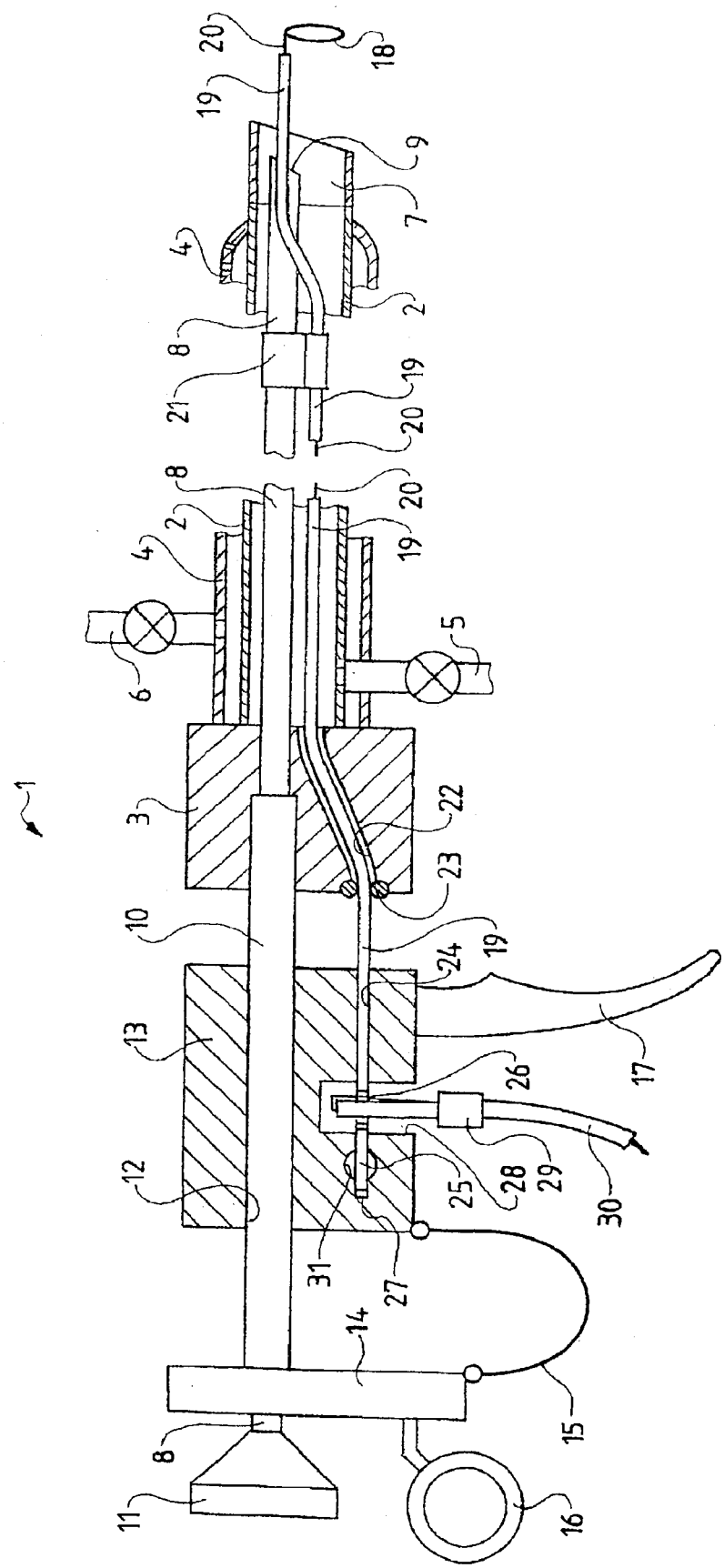

UROLOGICAL ELECTROSURGICAL RESECTOSCOPE

BACKGROUND OF THE INVENTION

Urological resectoscopes are primarily used for prostate resections, though, depending on the particular design, they also may be used for other surgical purposes. Herein the concept of "resectoscope" denotes endoscopic instruments wherein an optics and an electrode support, together with a distal electrode, are configured in a stem tube and wherein the electrode support jointly with the electrode is configured in an axially displaceable manner. The support is affixed at its proximal end to a resectoscope slide block with which it makes electric contact, the slide block being axially displaceable by manually driving a grip in order to axially displace the electrode.

During prostate resection, the distal stem tube end of the resectoscope is advanced through the urethra inside the prostate. When hf is applied to the electrode, the electrode may be advanced and retracted by manually driving the slide block in order to cut tissue. In general, the electrode is configured as a wire loop to trim tissue snippets. Furthermore, the electrode may assume other geometries, for instance being a button electrode, a roller electrode, a knife electrode or the like, in order to allow application to different purposes, such as coagulation, cutting or the like.

Problems are encountered as regards the appropriate contact between the electrical conductor feeding the electrode and the slide block site it touches. At this contact zone of the conductor, the contact must be implemented by a further cable leading to a separate hf generator. HF loaded contacts are problematical and are susceptible to defects or damage, such as scorching.

In older designs, a tightening screw simultaneously sets up the contact and the mechanical affixation of the electrode support inside the slide block. Once such a contact site chars, the full slide block must be replaced.

The WO 96/234449 patent document, as shown by its FIG. 16, which is outside the species discussed herein, concerns a bipolar-electrode resectoscope. In other words, two electrical conductors cross the electrode support. Consequently, the electrode support is fitted with two contact zones in the region of the slide block. A plug-element affixed to the slide block and fitted on the continuing cable implements contact both contacting zones and, hence, simultaneously implements the contacting function and mechanical clamping. A special and separate fastener is not provided. Accordingly, in this design contacting and clamping will always be simultaneous. This design precludes affixing the electrode support, for the purpose of testing the mechanical operation, prior to setting up the contact(s).

A design of the kind disclosed herein is known from U.S. Pat. Nos. 4,917,621 and 4,919,131, each shown in their particular FIG. 3. The slide block therein is fitted with a transversely continuous duct receiving the continuing hf cable's plug element, which makes contact with the electrode support's contact zone freely resting in the duct. A clamping element is present distally from the duct and acts on a fastening segment of the electrode support.

This design offers the advantage to separately affix in mechanical manner the electrode support and the clamping element on the slide block, as a result of which it is possible to first check this slide block's proper mechanical operation. Thereupon, contact may be implemented with the plug. If the contact site should char, only the electrode support and the cable together with the plug need be changed. The clamping element and the slide block on the other hand remain intact because the clamping element is separate.

However, the known design of the above species does entail drawbacks.

Because the affixation device is configured distally from the contacting element, the electrode support site where affixation takes place is crossed by the electric conductor connecting the contacting site to the electrode. As a result the electrode support lacks mechanical strength in this region. The affixation device must allow for this lack of strength and illustratively may only operate with minute tightening forces. If affixation takes place by means of a slide block entering a groove and acting on the electrode support, then the groove may only be very shallow and consequently the reliability of affixation is considerably reduced.

The proximal end zone of the electrode support is constituted both by that zone wherein affixation takes place and by the contacting zone. These zones, namely the full end zone of the electrode support, therefore are rigid and more resistant to bending than the remainder of the electrode support, which consists only of an inner conductor and an outer insulation. In resectoscopes, however, the electrode support typically will be configured tightly against the optics inside the stem tube, whereas, in the region of the slide block, the support and optics must be farther apart in order to subtend enough space for the contacting system and the affixation device. Therefore, the electrode support must be pivotably supported inside the main block in the manner indicated, for instance, in FIG. 3 of the patent document WO 96/234449. However, the main block being required to be of moderate length on technical grounds, large pivoting must take place over a short path. Unfortunately, the considerable length of the rigid end region of the known electrode supports hampers such motion.

Moreover, assembly may be defective if the electrode support was insufficiently inserted and thereupon was fixed in place.

SUMMARY OF THE INVENTION

It is an objective of the present invention to create a resectoscope of the above-mentioned species that allows affixing the electrode support in a problem-free manner in the slide block and to appropriately make electrical contact with it.

In the invention, the affixation element is configured proximally relative to the contacting element. Accordingly, the design of the invention requires an electrode support of which the affixation site is located proximally relative to the contact zone. As a result the electrode support's affixation zone no longer need be crossed by an inner electric conductor and, hence, may be made mechanically very strong, for instance being a solid metal piece. A number of different and very effective affixation methods may be used, for instance clamping with very high clamping forces, locking into deep grooves or even locking using a pin passing through the electrode support. Furthermore, firmly retaining detent connections may be used. The proximal configuration of the affixation element offers a further advantage, namely that upon proper affixation it assures complete insertion of the electrode support. That is, it will then be situated at the site of the contacting element of the electrode support's contact zone and as a result contact will also be assured. Lastly, this design of the invention also allows solving the problem of pivoting the stiff end segment of the electrode support when being inserted into the main block. The bending-resistant end piece, which consists of the contact zone and the affixation zone, may now be shorter. Again, the electrode support's affixation zone may assume a lesser diameter, and thereby enabling tighter pivoting.

In further accordance with the present invention, the limit stop may be in the form of the end of the receiving borehole in the slide block. The inserted electrode support may be advanced as far as the stop and then will be situated highly accurately by its affixation zone against the affixation element and by its contact zone against the contact element. The affixation element itself, for instance a tightening screw, a tightening slide block or a detent element, may also be fitted with a limit stop.

BRIEF DESCRIPTION OF THE DRAWING

These and further features of the invention will be apparent with reference to the drawing, wherein the resectoscope according to the present invention is diagrammatically shown in the form of an axial section with assembled electrode.

DETAILED DESCRIPTION OF THE PREFERRED EMBODIMENT

The shown resectoscope 1 comprises a stem tube 2 that is affixed by its proximal end to a main block 3. In manner not shown in the drawing, the stem tube 2 may be detachably mounted by means of a conventional coupling element on the main block 3. An external tube 4 encloses the stem tube 2 and also is mounted on the main block 3, again in conventional manner, using a coupling element (not shown). The inside of the stem tube 2 serves in conventional manner as an intake duct for permanent irrigation and, as shown in the drawing, is externally accessible through a valve-fitted hookup 5, which may be connected to a hose. Another and similar hookup 6 connecting a further hose is connected to the annular gap between the stem tube 2 and the external tube 4 and serves as the return duct.

The two tubes 2 and 4 are conventionally metallic. The distal end zone of the stem tube 2 is conventionally insulating and illustratively in the form of a ceramic element 7.

An optics 8 runs axially inside the stem tube 2 and, in the shown assembled configuration, views by its distal objective 9 the field of surgery ahead of the ceramic end element 7, while proximally it runs through the main block 3. From the latter position it runs through a guide tube 10 affixed in the main block 3 and terminates on the other side of the proximal end of the tube 10 into an ocular 11, which may be replaced by a camera.

By means of a guide borehole 12, a slide block 13 rests in an axially displaceable manner on the guide tube 10. An end plate 14 is affixed to the proximal end of the guide tube 10 and, by means of a conventional leaf spring 15, resiliently braces the slide block 13. A thumb ring 16 is mounted on the end plate 14, and a finger grip 17 is mounted on the slider 13. Using one hand, the surgeon by means of the thumb and index finger can actuate the thumb ring 16 and the finger grip 17 and thus may axially displace the slide block 13. Alternatively, the just discussed "active" function may be replaced by a "passive" function wherein the leaf spring 15 is configured between the slide block 13 and the main block 3 and the drive sites 16, 17 also are situated at these components.

The shown resectoscope includes an exchangeable, hf-loaded electrode 18, which is of conventional design with respect to prostate resection. Namely, the electrode is in the form of a wire loop of which the plane is orthogonal to the axial direction. The electrode 18 is supported by an electrode support 19 in the form of an inner conducting wire 20 enclosed by an external insulation. In a conventional manner, this electrode support 19 rests by means of a sleeve 21 in longitudinally displaceable manner on the optics 8 and runs through the stem tube 2 as far as the main block 3. From there it runs through a laterally deviated transmission duct 22 fitted with O rings 23 or the like to seal off the liquids, next running from the duct's proximal mouth again parallel to the axis but at a larger distance from it into a seating borehole 24 in the slide block 13. In an alternative embodiment, the seating borehole 24 may be replaced for instance by a proximally conically converging aperture, or a sideways open slot, or the like, to seat the electrode support 19.

In its proximal end zone, the electrode support 19 comprises an affixation zone 25 constituting its end element. The affixation or end zone 25 is appropriately mechanically strong, for instance being made of solid metal in order to allow reliably mechanically affixing the electrode support at that site. Distally from the affixation zone 25, the electrode support 19 adjoins a contact zone 26 fitted with an electrically conducting outside surface that is connected in electrically conducting manner with the conducting wire 20 of the electrode support 19.

In the form of its proximal end 27, the seating borehole 24 further comprises a limit stop for the electrode support 19 that can be inserted in the proximal direction in the seating borehole 24 as far as the stop.

When, in the shown assembly, the electrode support 19 has been inserted in the seating borehole 24 of the slide block 13 as far as the limit stop 27, then it is situated with its contact zone 26 in a clearance 28 of the slide block 13 wherein the contact zone 26 is freely accessible from the outside. In that configuration, the electrode support 19 may be contacted for instance by the shown clamping plug 29 at the end of a cable 30 running to an hf generator (not shown).

An affixation element, which in this embodiment comprises a transverse borehole 31, is configured directly proximally next to the clearance 28 in the region of the affixation zone 25 of the electrode support 19 in the slide block 13 and illustratively is fitted with an inside thread to allow screwing-in a tightening screw. Alternatively, the affixation element also may be of another design, for instance including a slider engaging a groove, or in the form of a snap-in connection or the like.

As shown, the clearance 28 may offer omnidirectional, free access to the contact zone 26 of the electrode support 19, however, and in illustrative manner, it may also be designed as a cavity accessible only from one side as disclosed for instance in U.S. Pat. No. 4,919,131.

Once the electrode support 19 is appropriately affixed in the slide block 13 and makes appropriate electrical contact, then, by means of the above displacement of the slide block 13, the entire electrode support 19 together with the electrode 18 may be displaced longitudinally relative to the stem tube 2. Thereupon, by observation through the optics 8 and applying hf to the electrode 18, the electrode may be used for cutting while moving axially.

The clamping plug 29 will be removed and the affixation element (transverse borehole 31) will be loosened when the electrode 18 must be exchanged. Thereupon, the electrode support may be fully extracted in the distal direction from the resectoscope 1. On the other hand, a new electrode may be inserted in the proximal direction as far as the limit stop 27, then mechanically affixed and electrically contacted. The electrode support 19 may be first mechanically affixed to the transverse borehole 31 and its proper operation may be tested by displacing the slide block 13 to and fro before electric contact is implemented with the clamping plug 29.

In the shown embodiment, the electrode support 19 bears an electrode 18 in the form of a conventional resectoscope loop. However electrodes of different geometries from that of the shown electrode may be used, for instance button electrodes, pin electrodes, roller electrodes or knife electrodes, which when loaded with hf shall function in coagulating, vaporizing or cutting manner.

Illustratively, bipolar electrodes also may be used, where the electrode support 19 therefore will bear two electrodes each of which shall be connected to one of the two output terminals of an hf source. In this instance two electrically conducting wires 20 must be used inside the insulating electrode support 19. Again, instead of using the above shown contact zone 26, in the latter case two contact zones must be used at the proximal end of the electrode support and, illustratively, will be contacted by a double clamping plug.

The shown embodiment provides the end 27 of the seating borehole 24 as the limit stop regarding the insertion of the electrode support 19. However, a limit stop also may be configured at the clamping element itself, for instance at the tightening screw that shall be screwed into the threaded borehole 31. If, for instance, a slider engaging a groove in the affixation zone 25 were used as the clamping element, then the slider as well may be fitted with an appropriate stop cooperating in a suitable way, for instance with a matching stop on the affixation zone 25.

The illustrated embodiment of the invention shows that the electrode support 19 appropriately mounted in the slide block 13 is configured in a clearance 28 from which the support 19, at its contact zone 26, is freely externally accessible in order that, again as shown, it may be made to contact an externally introduced connector 29. However, other contacting elements also are feasible, where, for instance, the contact zone 26 touches a contact affixed for instance in the slide block 13 and which is connected to a cable in a way different from that shown that extends the transmission. In such a design the clearance 28 may be omitted.

What is claimed is:

1. A urological resectoscope (1) comprising an axial stem tube (2) having a distal end and a proximal end, said proximal end of said stem tube being affixed to a main block (3), a slide block (13) being supported proximally of said main block in an axially parallel displaceable manner relative to said main block (3), said slide block (3) being fitted with a seat (24), an affixing element (31) and an electrically contacting means (28, 29), said resectoscope further comprising within it an hf-loaded electrode (18) which is associated with an electrode support (19) that is fitted with an electrically conducting wire (20) enclosed by an external insulator, said electrode (18) being supported so as to be axially displaceable beyond the distal end (7) of the stem tube (2), where the electrode support (19), when in an assembled resectoscope, running through the stem tube (2) and the main block (3) and into the seat (24), is affixed by the affixing element (31) and can be made to contact the electrically contacting means (28, 29), wherein the affixing element (31) is configured proximally relative to the electrical contacting means (28, 29) at the slider block (13) and wherein the electrically contacting means (28, 29) is disposed within the slider block and relatively between the affixing element (31) and the main block (3).

2. The resectoscope as claimed in claim 1, wherein a limit stop (27) for the electrode support (19) is provided in a region of the affixing element (31).

3. A urological resectoscope (1) comprising:
  (a.) a viewing device (11);
  (b.) a main block (3);
  (c.) an axial stem tube (2) having a distal end and a proximal end, said proximal end of the stem tube being affixed to the main block (3);
  (d.) a slide block (13) disposed between the viewing device (11) and the main block (3) and having a passage (24) formed therein, said slide block (13) being axially movable relative to the main block (3);
  (e.) an electrode support (19) comprising an electrically conducting wire (20) enclosed by an external insulator, said electrode support (19) running through the stem tube (2) and the main block (3) and into the passage (24) of the slide block (13);
  (f.) an hf-loaded electrode (18) supported by the electrode support (19) so as to be axially movable beyond the distal end of the stem tube (2);
  (g.) affixing means (31) for releasably securing an affixation zone of the electrode support (19) to the slide block (13);
  (h.) electrically contacting means (28, 29) for contacting a contact zone of the electrode support (19) so as to establish an electrical connection with the electrically conducting wire (20); and
  (i.) wherein the affixation zone of the electrode support (19) is disposed between the contact zone of the electrode support (19) and the viewing device.

4. The urological resectoscope (1) of claim 3, wherein the electrode support (19) further comprises an electrically conducting outside layer in electrical contact with the electrically conducting wire (20), said electrically conducting outside layer being located at the contact zone.

5. The urological resectoscope (1) of claim 3, wherein the affixing means comprises a screw threadably disposed in a transverse borehole formed in the slide block (13).

6. The urological resectoscope (1) of claim 3, wherein the electrically contacting means comprises a clamping plug extending through an opening formed in the slide block (13).

* * * * *